United States Patent
Joseph et al.

(10) Patent No.: US 8,257,323 B2
(45) Date of Patent: Sep. 4, 2012

(54) CANNULA SYSTEM AND METHOD

(75) Inventors: Katherine Rose Joseph, Rockford, MI (US); David B. DeWindt, Grand Rapids, MI (US); Rebecca L. Engel, Kalamazoo, MI (US); Donald R. Sandmore, Newaygo, MI (US); David E. Weston, Rockford, MI (US); John Mrachek, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1208 days.

(21) Appl. No.: 11/195,913

(22) Filed: Aug. 3, 2005

(65) Prior Publication Data
US 2007/0038170 A1 Feb. 15, 2007

(51) Int. Cl.
*A61M 5/32* (2006.01)
(52) U.S. Cl. ............. 604/272; 604/104; 604/96.01
(58) Field of Classification Search ............ 604/272, 604/104, 96.01, 103.06, 103.08, 101, 916
See application file for complete search history.

(56) References Cited

U.S. PATENT DOCUMENTS

| | | | |
|---|---|---|---|
| 3,136,316 A | 6/1964 | Beall | |
| 4,129,129 A | 12/1978 | Amrine | |
| 4,391,276 A * | 7/1983 | Lazarus et al. | 604/266 |
| 4,548,597 A | 10/1985 | Nelson | |
| 4,596,548 A | 6/1986 | DeVries et al. | |
| 4,639,252 A | 1/1987 | Kelly et al. | |
| 4,804,359 A | 2/1989 | Grunwald et al. | |
| 4,863,441 A | 9/1989 | Lindsay et al. | |
| 5,041,084 A | 8/1991 | DeVries et al. | |
| 5,171,218 A | 12/1992 | Fonger et al. | |
| 5,769,828 A | 6/1998 | Jonkman | |
| 5,817,071 A | 10/1998 | Dewindt et al. | |
| 6,042,576 A | 3/2000 | DeVries | |
| 6,146,371 A * | 11/2000 | DeWindt et al. | 604/506 |
| 6,159,178 A * | 12/2000 | Sharkawy et al. | 604/103.08 |
| 2002/0107506 A1 | 8/2002 | McGuckin et al. | |
| 2005/0063860 A1 | 3/2005 | Carpenter et al. | |

FOREIGN PATENT DOCUMENTS

| | | |
|---|---|---|
| DE | 195 12 607 | 10/1996 |
| WO | 01/21249 | 3/2001 |

OTHER PUBLICATIONS

International Search Report for International Application No. PCT/US2006/030353 mailed Feb. 20, 2007 (6 pages).

* cited by examiner

*Primary Examiner* — Kevin C. Sirmons
*Assistant Examiner* — Phillip Gray (57) ABSTRACT

Embodiments of the invention provide a cannula having a body with a first outer diameter, a proximal end, a distal end, a lumen extending between the proximal and distal ends, and a portion outward of the first outer diameter having a second outer diameter greater than the first outer diameter that is adapted to space tissue from the fluid inlet to maintain fluid flow. Such a cannula is particularly useful for cardiopulmonary bypass procedures using a kinetically assisted venous drainage system.

18 Claims, 16 Drawing Sheets

CANNULA SYSTEM AND METHOD

FIELD SECTION

The disclosure relates to a cannula system and method, and more particularly to a cannula having an outward portion adapted to space tissue from a fluid inlet to maintain fluid flow.

BACKGROUND SECTION

Cannulae have a wide variety of applications during surgical procedures. For example, in coronary surgery, venous and arterial cannulae are used to conduct fluids such as blood between the body and bypass equipment. Cannulae are used to conduct cardioplegia solution for both antigrade and retrograde solution administration, and cannulae are also used as vents, sumps, and for chest tube fluid suction.

A recent trend in surgical procedures, such as cardiopulmonary bypasses, is to utilize a kinetically assisted venous drainage system, such as that sold as The Resting Heart™ System by Medtronic and described in U.S. Patent Application Publication 2005/63860, the content of which is hereby incorporated by reference. Such a system increases suction on the drainage cannula relative to traditional vacuum assisted venous drainage and gravity venous drainage systems. Such increased suction may cause the fluid inlets to come into contact with and be occluded by surrounding tissue, thereby reducing fluid flow.

BRIEF SUMMARY SECTION

Embodiments of the invention include a cannula having a cannula body with a first outer diameter, a proximal end, a distal end, and a lumen extending between the proximal and distal ends. A fluid outlet may be formed on the proximate end, and at least one fluid inlet may be formed proximal of the distal end. In some embodiments, the cannula includes a portion outward of the first outer diameter having a second outer diameter greater than the first outer diameter that is adapted to space tissue from the fluid inlet. Such a cannula is useful for maintaining fluid flow by reducing occlusion of the fluid inlet by surrounding tissue, particularly in procedures using a kinetically assisted venous drainage system. Embodiments of the invention also include methods of reducing cannula fluid inlet occlusion.

DETAILED DESCRIPTION OF THE ILLUSTRATED EMBODIMENTS

The following discussion is presented to enable a person skilled in the art to make and use the embodiments of the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives that fall within the scope of the invention.

Figure 1:
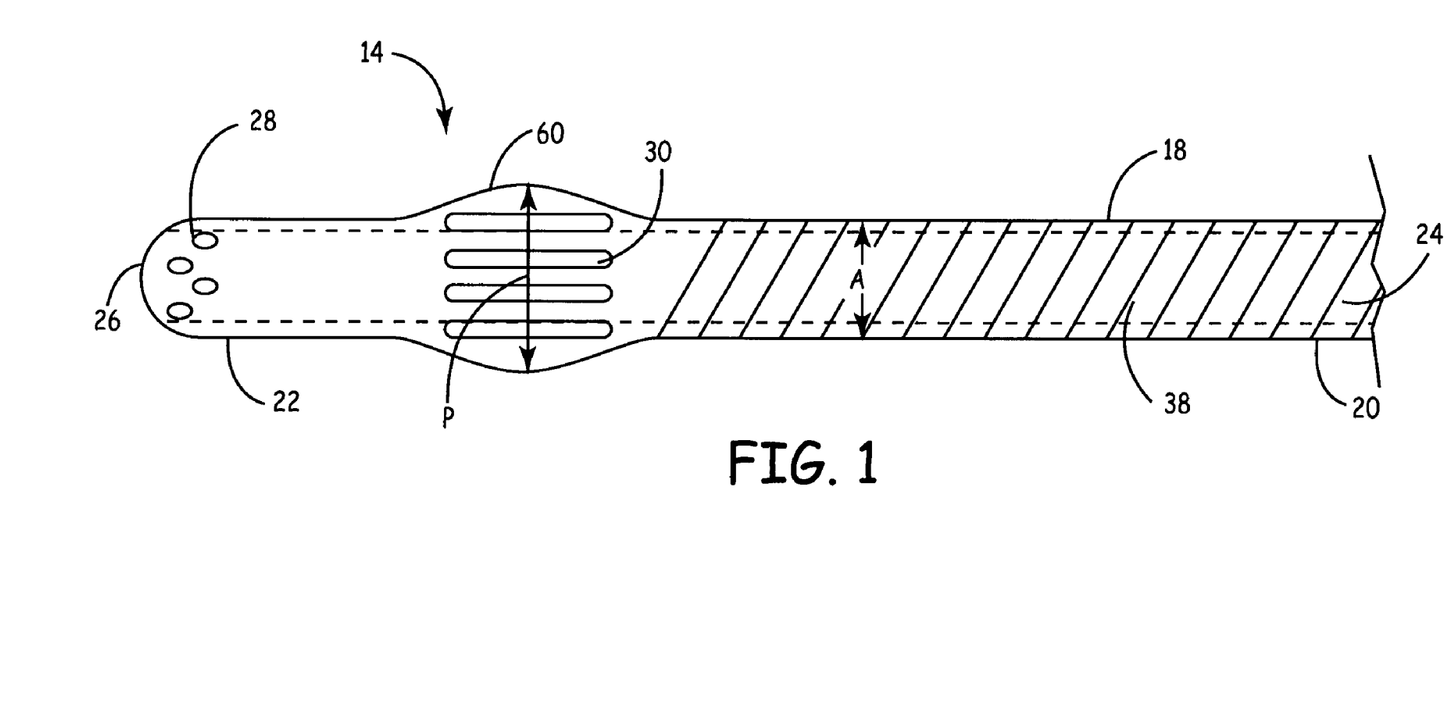
FIG. 1 is a side plan view of a cannula according to an embodiment of the invention.
Figure 3:
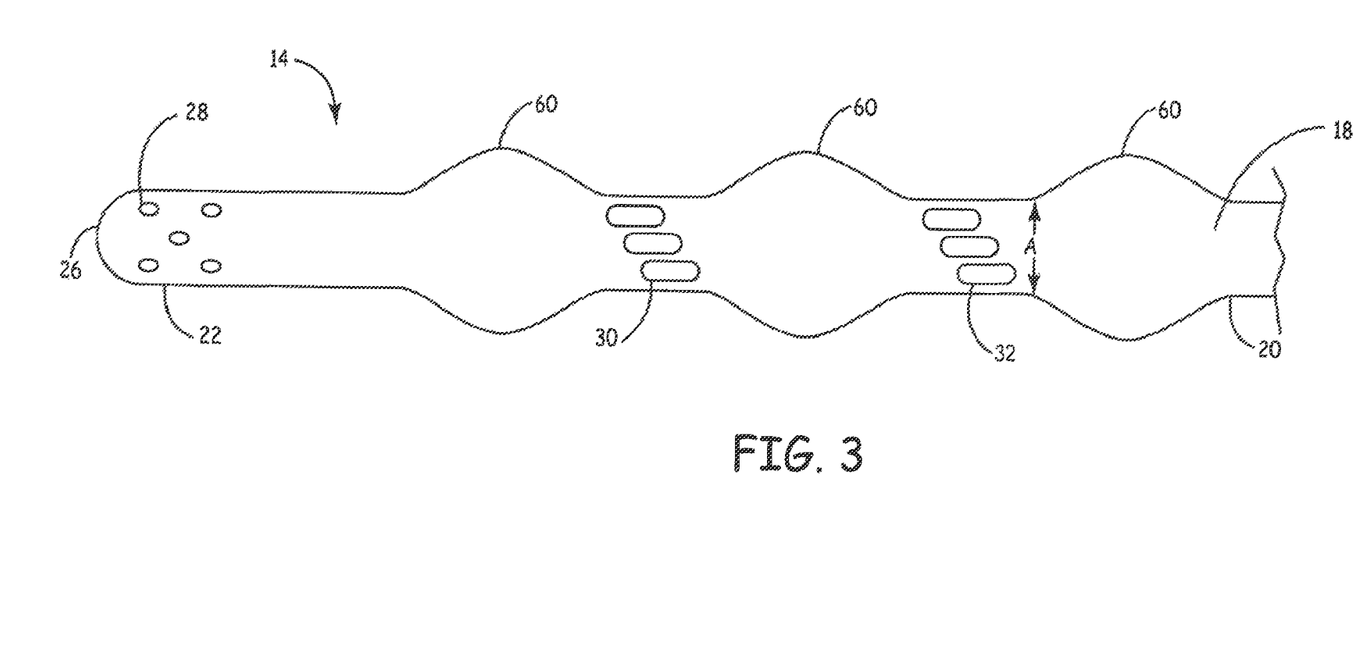
FIG. 3 is a side plan view of a cannula according to an embodiment of the invention.

As shown in FIG. 1, some embodiments of the invention include a cannula 14. The cannula 14 comprises a cannula body 18 having a proximal end 20, a distal end 22, a lumen 24 extending between the proximal and distal ends, and a tip 26. The cannula body also includes a first outer diameter A. The tip 26 may include at least one tip fluid inlet aperture 28 for the receipt of fluid into the lumen. As shown in FIG. 1, some embodiments include a first set of fluid apertures 30 formed proximal the distal end 22. Additional sets of fluid apertures, such as a second set of apertures 32, as shown in FIG. 3, may be provided at other spaced distances proximally from the distal end. Additional sets of apertures may be provided, such as three, four, or more apertures sets. A helically wound reinforcing spring 38 may be integrally formed into the cannula body 18.

Figure 2:
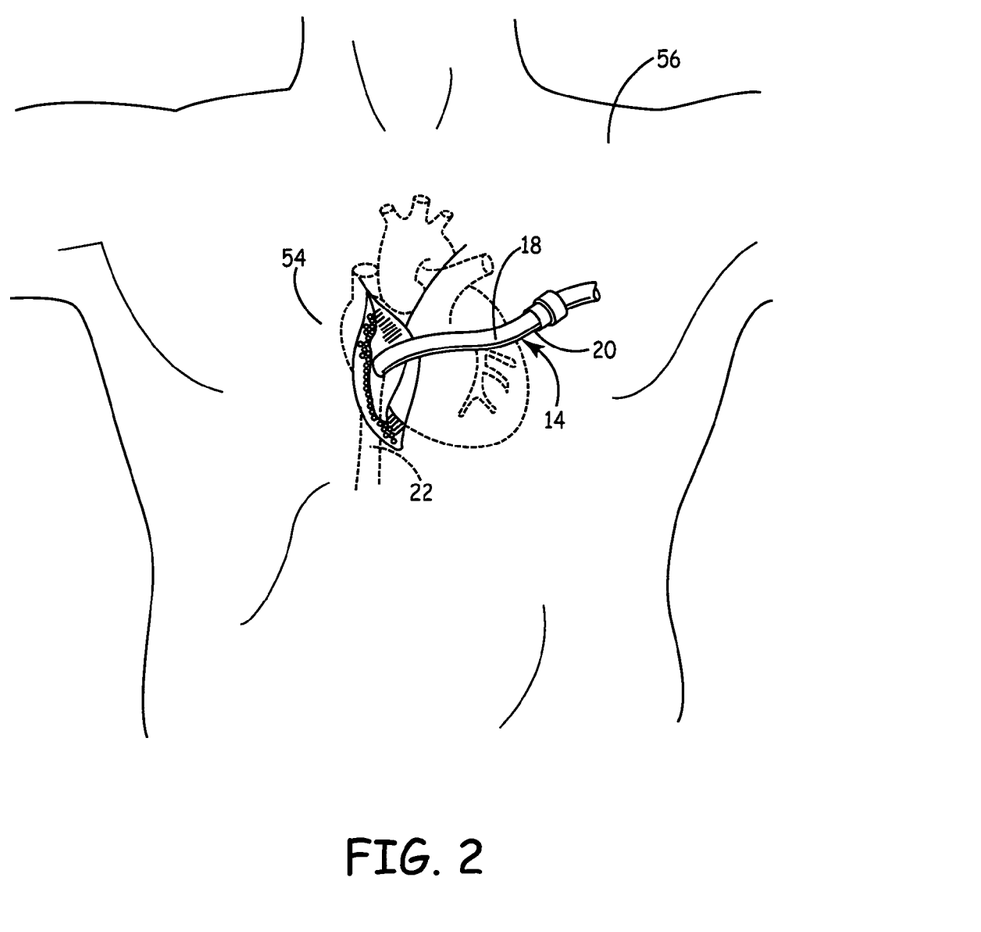
FIG. 2 is a plan view of a patient showing a cannula according to the invention passing through a mini-thoracotomy.

As shown in FIG. 2, embodiments of the cannula 14 may be suited for use as a venous cannula during a coronary surgical procedure, such as by being inserted through the chest wall 54 of a patient 56. In use, the cannula 14 may be inserted through an appropriate incision into the right atrium and the inferior vena cava. As the distal end 22 of the cannula 14 is inserted into the blood flow passing through the right atrium and inferior vena cava, blood will enter the first set of fluid apertures 30 and the second set of fluid apertures 32, if present. Once the cannula 14 is properly positioned, the proximate end of the cannula 14 may be connected to any suitable bypass system, such as, for example, a kinetically assisted venous drainage system, a vacuum assisted venous drainage system, or a gravity venous drainage system. With the cannula 14 in this position, fluid (e.g., blood) enters the lumen 24 through both the first and second fluid apertures 30, 32 and is conducted to the bypass machine. In such a procedure, the tissue surrounding the first and second fluid apertures 30, 32 should be spaced from the apertures to avoid occluding them.

As shown in FIG. 1, some embodiments of the invention include a cannula having a portion 60 outward of the first outer diameter A having a second outer diameter P greater than the first outer diameter A. The portion 60 may be adapted to space tissue from the fluid inlet apertures 30 to maintain fluid flow during a surgical procedure. For example, the portion 60 may be useful for holding atrial tissue away from the apertures 30, thereby reducing the chance of aperture occlusion. The outward portion 60 may extend outward of the first outer diameter any distance suitable to space tissue and allow fluid flow. In some embodiments, the outer portion extends a minimum of about 0.030 inches (e.g., about 0.03 inches to about 0.385 inches) beyond the cannula body outer diameter A. As shown in FIG. 1, the first outer diameter A may generally be located on the main section of the cannula body proximal of the most proximal set of fluid inlet apertures, while the second outer diameter P may be generally located distally of the first outer diameter A.

Figure 4:
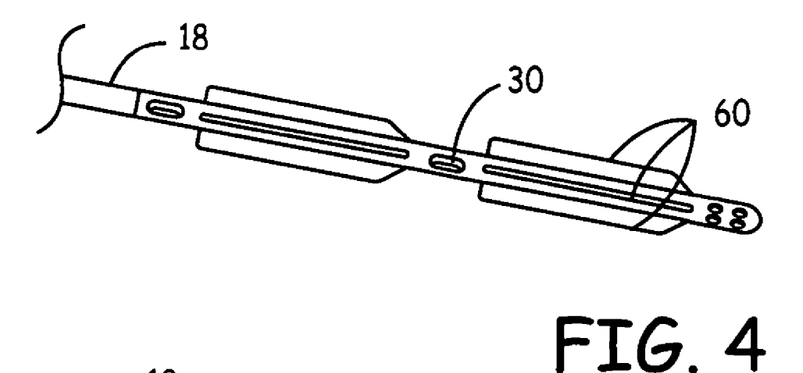
FIG. 4 is a side plan view of a cannula according to an embodiment of the invention.
Figure 5:
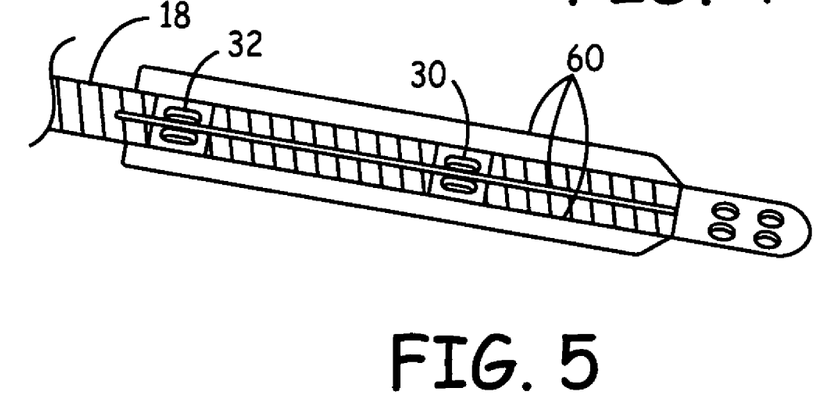
FIG. 5 is a side plan view of a cannula according to an embodiment of the invention.
Figure 6:
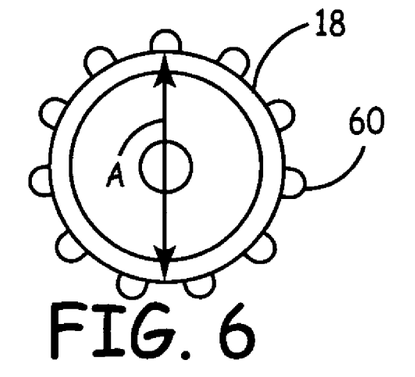
FIG. 6 is an end plan view of a cannula according to an embodiment of the invention.
Figure 8A:
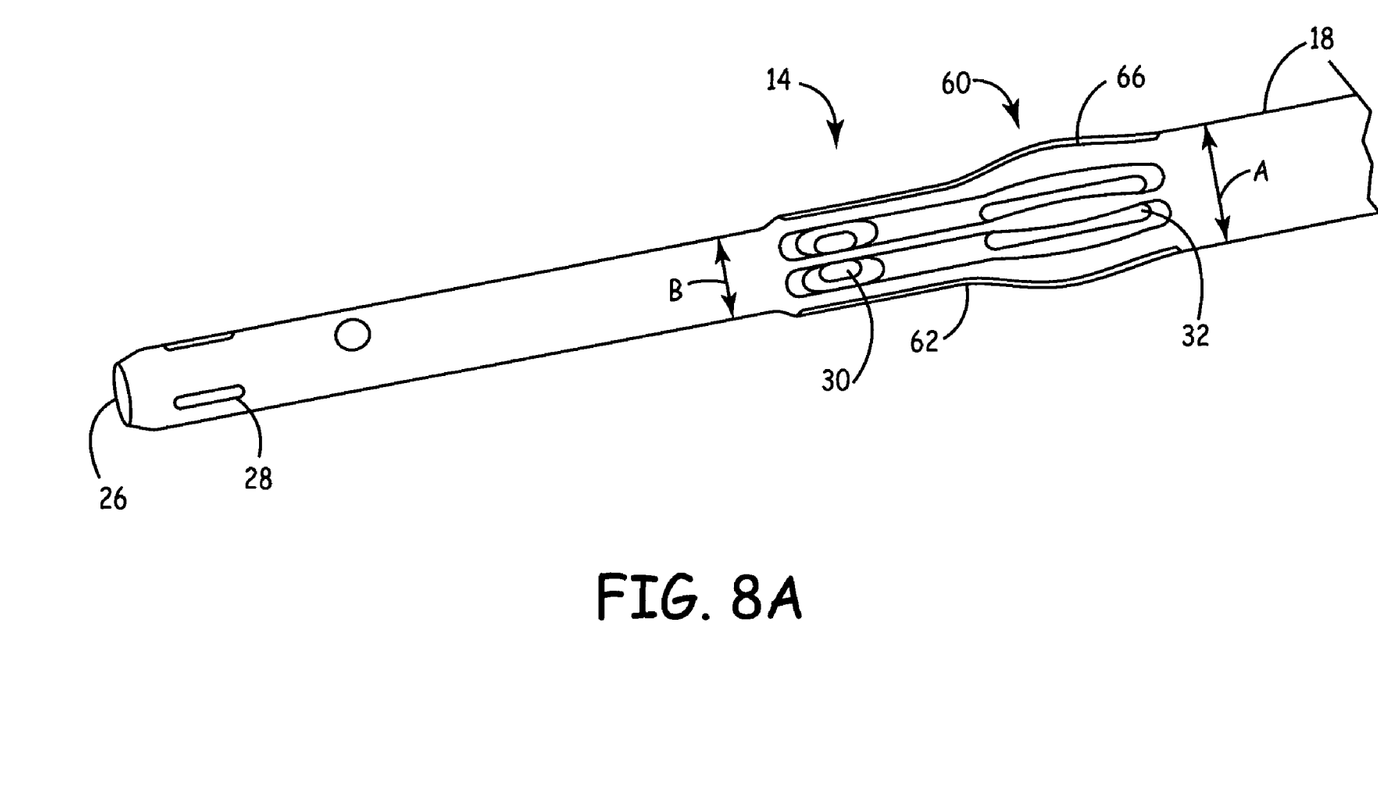
FIG. 8A is a perspective view of a cannula according to an embodiment of the invention.

Portion 60 may be placed along the cannula 14 in any position suitable to space tissue from and maintain fluid flow through the apertures. For example, as shown in FIG. 1, portion 60 may extend over and/or above a fluid inlet aperture set 30. In some embodiments, the portion 60 may be between the first fluid inlet 30 and a second fluid inlet 32, as shown in FIG. 4, and/or bookend the first or second fluid inlets, as shown in FIG. 3, or both bookend and be between the fluid inlets. The portion may also be continuous along the cannula body from distally of the first fluid inlet 30 to proximally of the second fluid inlet 32, as shown in FIG. 5, the end view of which is shown in FIG. 6. In such embodiments, the portion may also provide a channel for fluid flow between multiple sets of apertures. Further, the outer portion 60 can extend the full length of the cannula body that has been inserted into the patient, such as from the tip 26 to distally of the most distal set of apertures (e.g., second set 32) or any place(s) in between these points. In some embodiments, the cannula 14 has a tip diameter B that is less than the body diameter A, as shown in FIG. 8A. In such embodiments, the cannula may comprise a transition region 62 having a generally increasing diameter from the tip diameter B to the body diameter A. The fluid inlets 30 and/or the outer portion 60 may be located within the transition region 62.

Figure 7A:
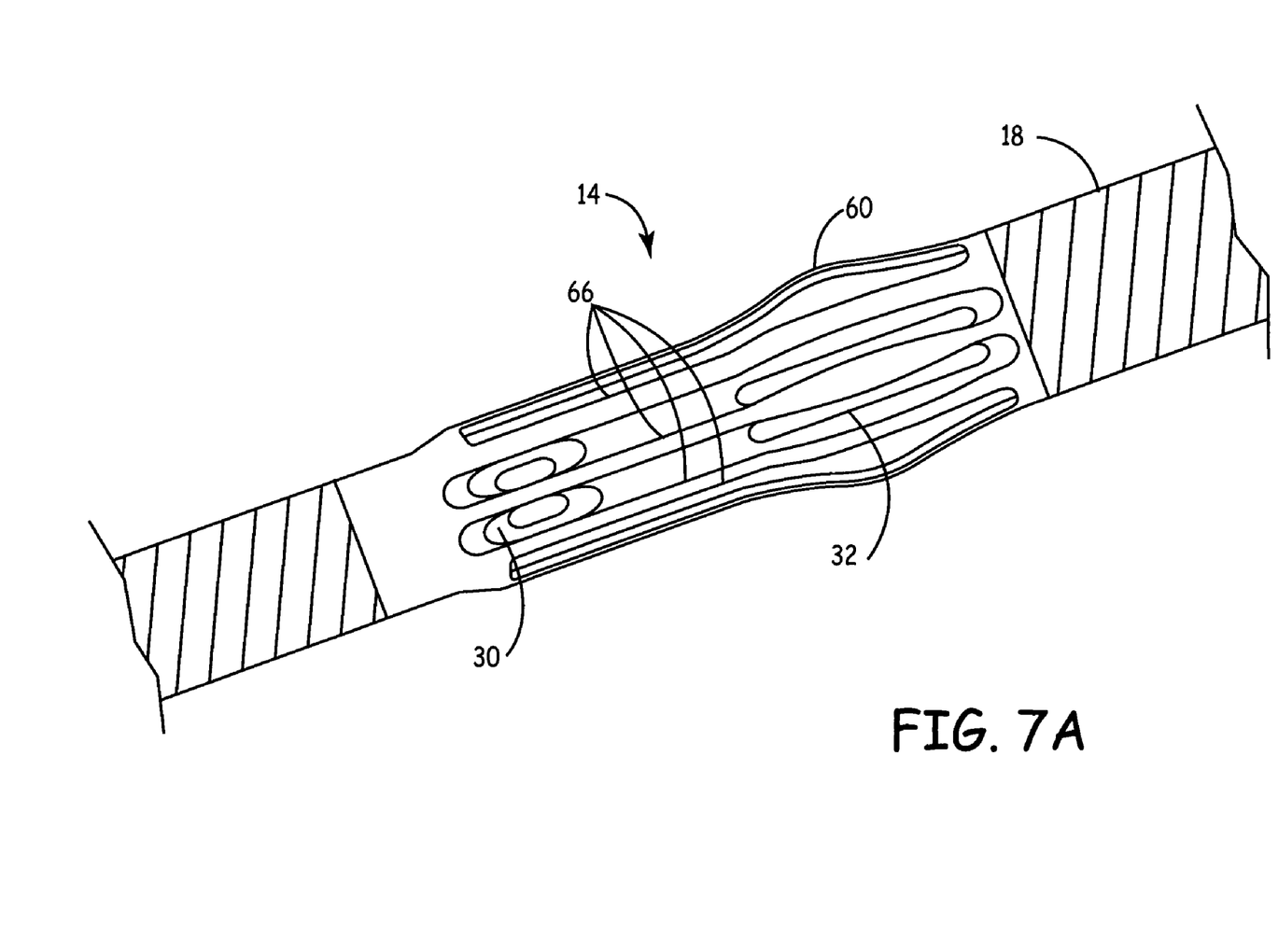
FIG. 7A is a perspective view of a cannula according to an embodiment of the invention.
Figure 7B:
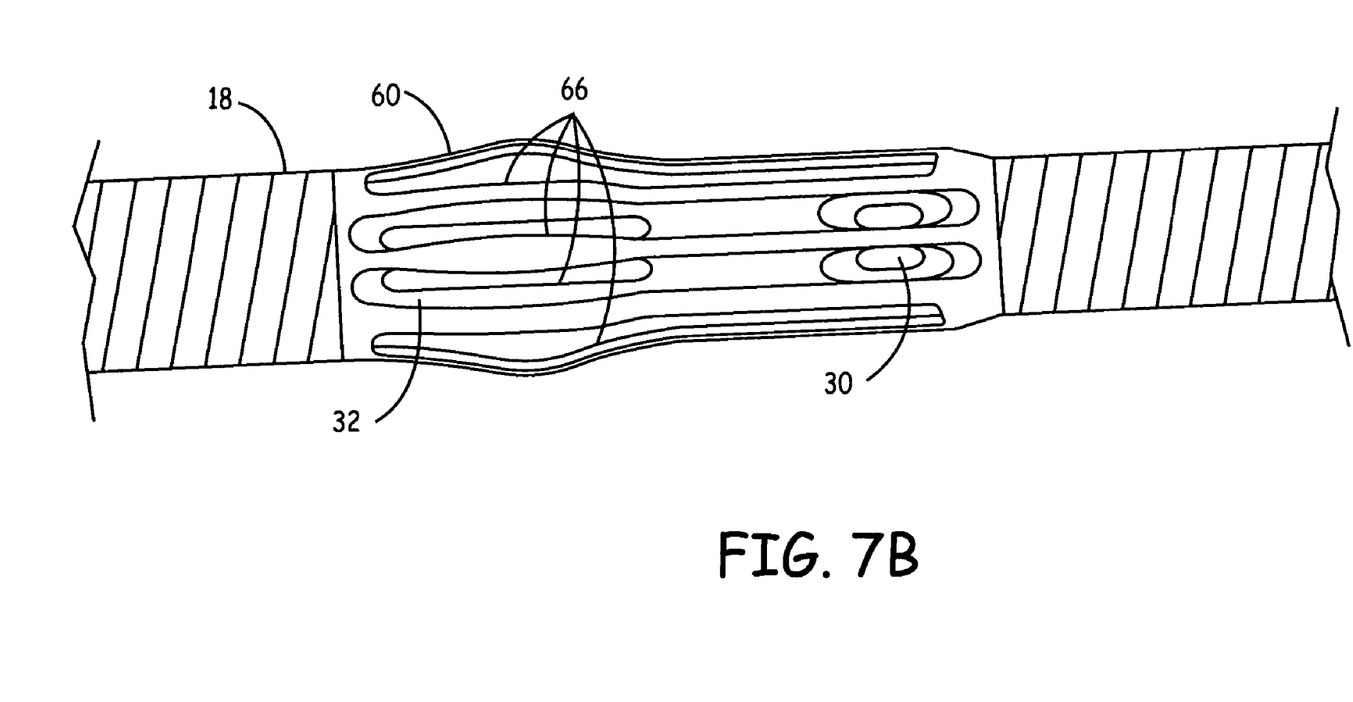
FIG. 7B is a perspective view of a cannula according to an embodiment of the invention.
Figure 7C:
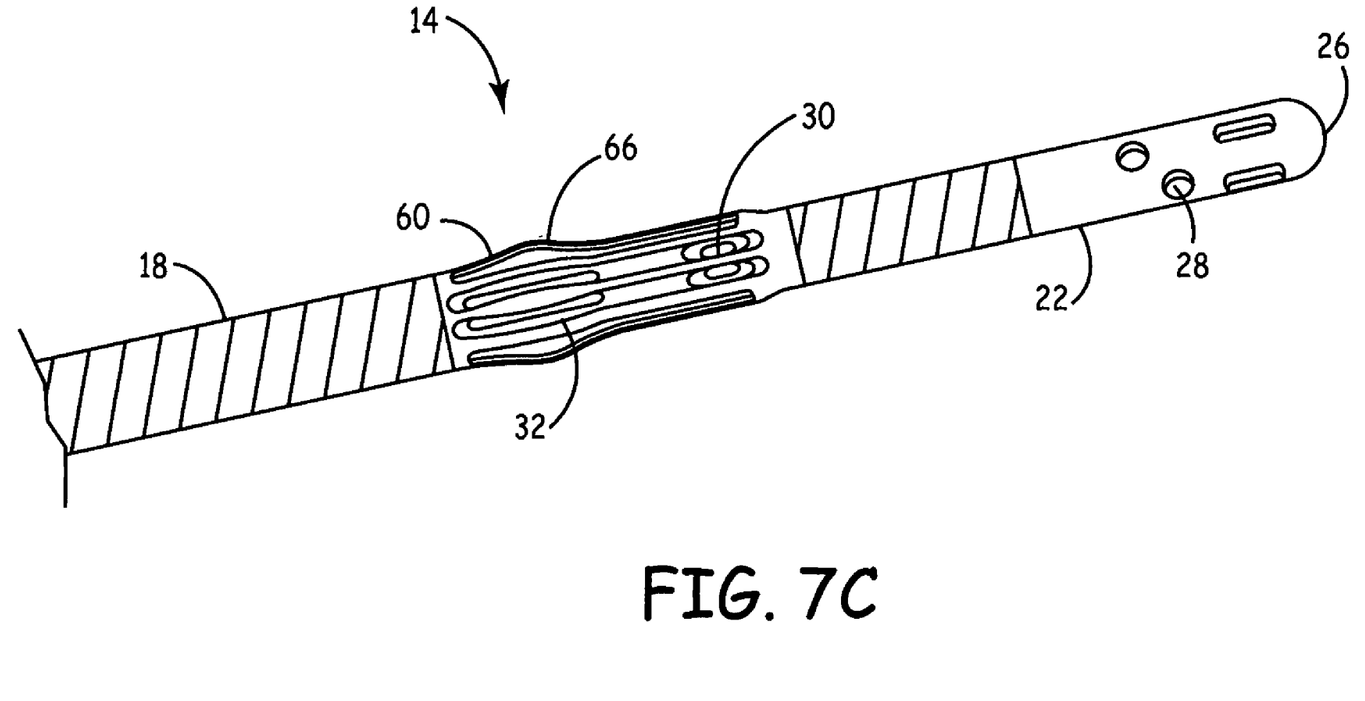
FIG. 7C is a perspective view of a cannula according to an embodiment of the invention.
Figure 8B:
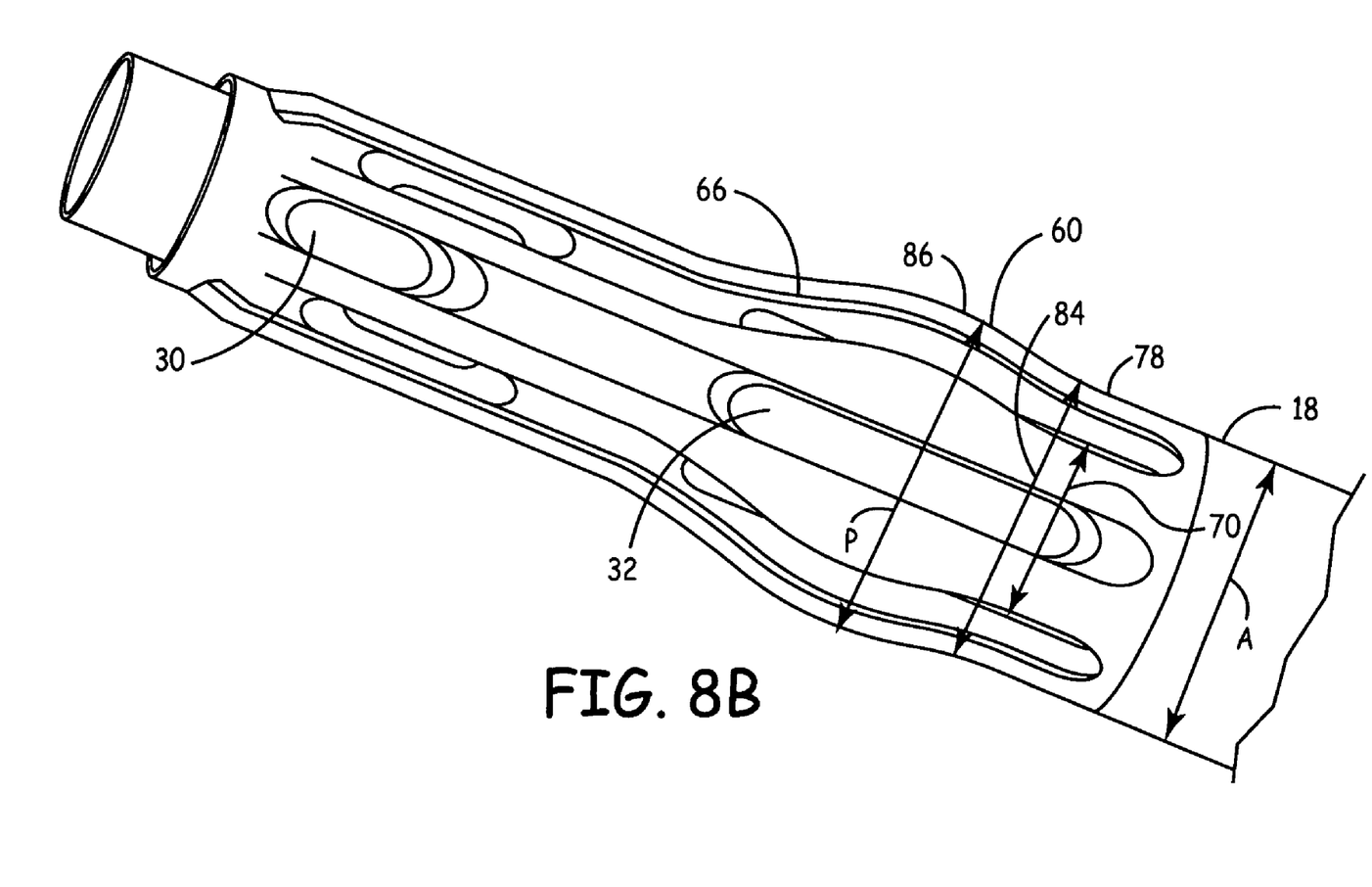
FIG. 8B is a perspective view of a section of a cannula according to an embodiment of the invention.
Figures 9, 10:
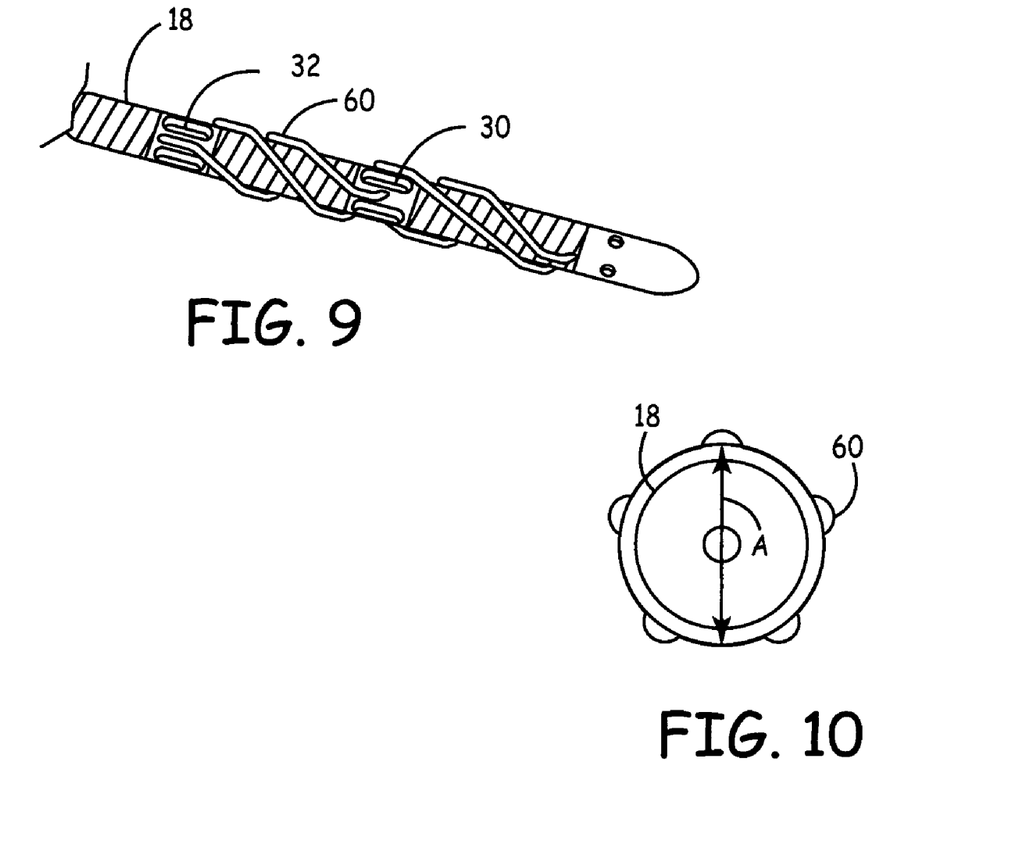
FIG. 9 is a side plan view of a cannula according to an embodiment of the invention.
FIG. 10 is an end plan view of a cannula according to an embodiment of the invention.
Figure 10A:
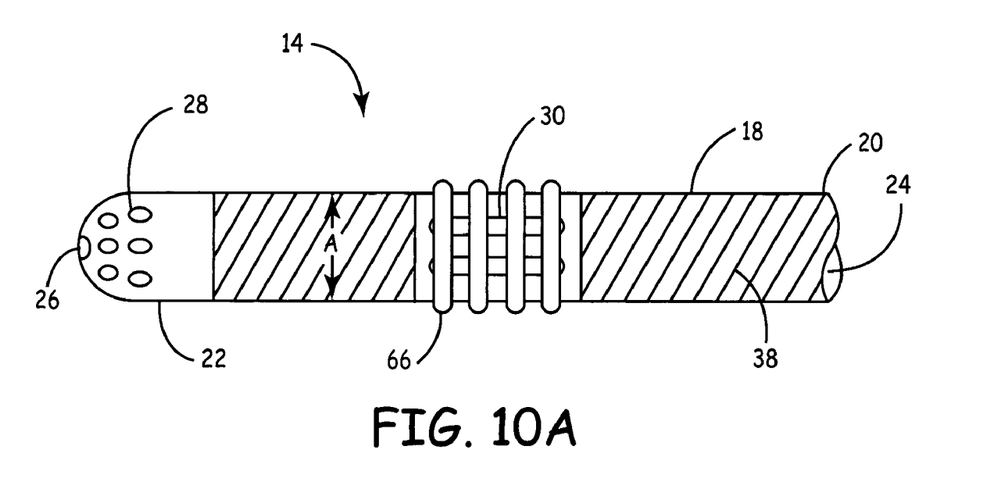
FIG. 10A is a side plan view of a cannula according to an embodiment of the invention.
Figure 11:
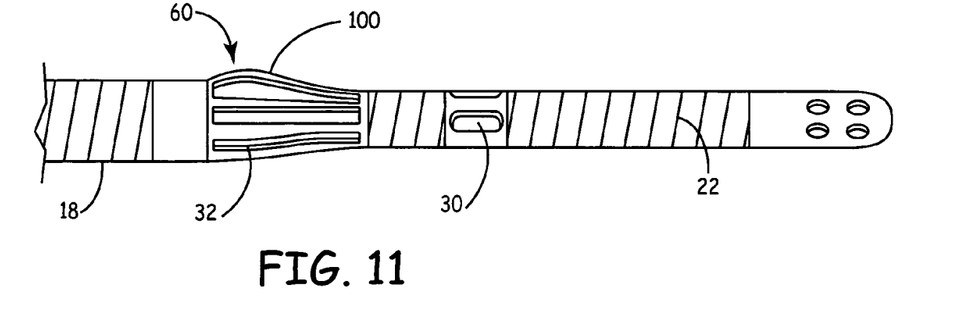
FIG. 11 is a side plan view of a cannula according to an embodiment of the invention.
Figure 12A:
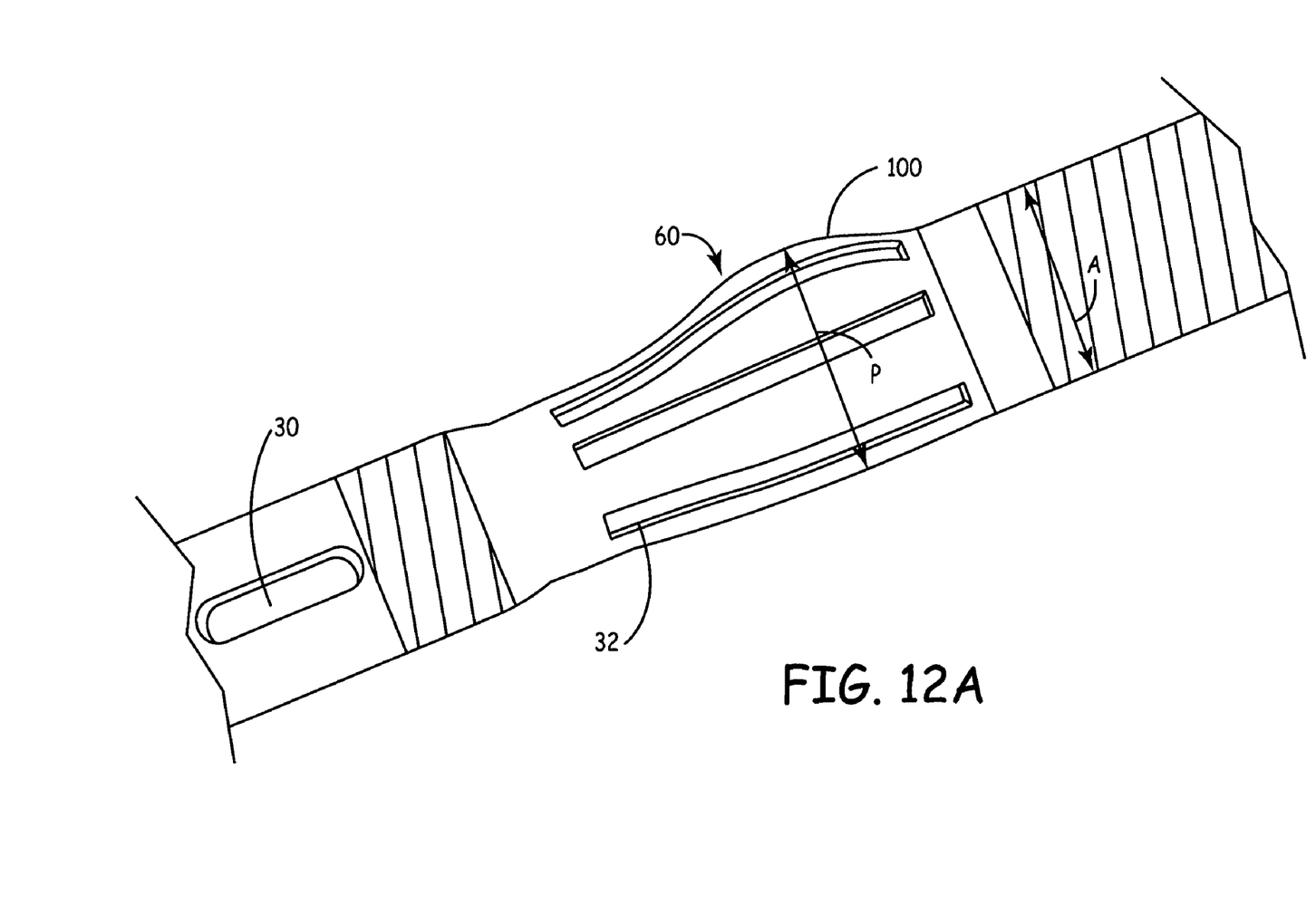
FIG. 12A is a perspective view of a cannula according to an embodiment of the invention.
Figure 12B:
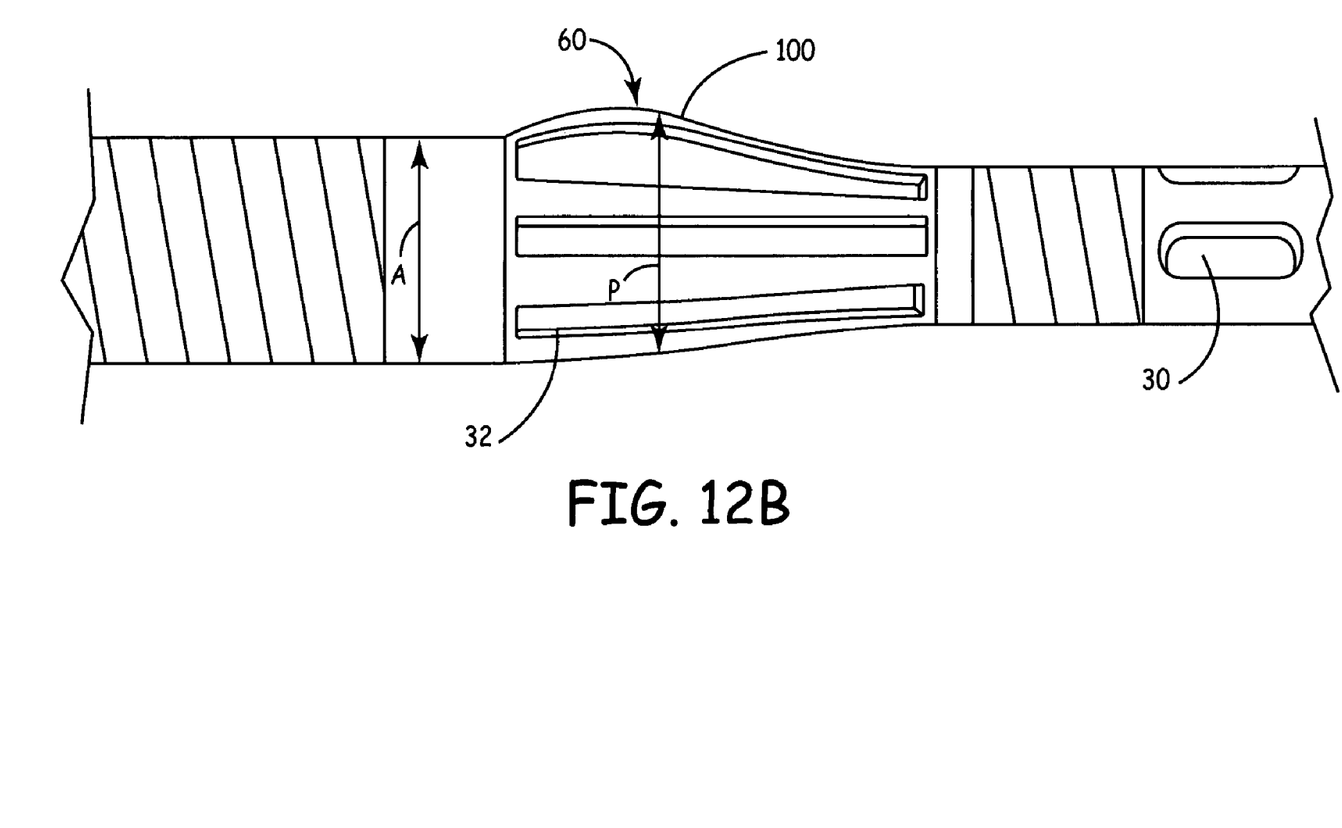
FIG. 12B is a side plan view of a cannula according to an embodiment of the invention.

The outward portion 60 may comprise any shape or feature suitable to prevent tissue from occluding fluid inlet 30 yet which allow fluids (e.g., blood), to flow through inlet 30. In some embodiments, the portion 60 outward of the first outer diameter includes a rib 66, as best shown in FIGS. 7A-C and 8A-B. Any suitable number of ribs may be provided (e.g., 6-10). Further, the ribs 66 may be symmetrical, as shown in FIGS. 7A-8B, or asymmetrical, as shown in FIGS. 11-12B. That is, each rib 66 may be substantially identical with respect to placement, shape, and/or size, or some ribs may be different than other ribs with respect to one or more of these attributes. The ribs 66 may also have any suitable orientation. For example, the ribs may have a longitudinal axis that is parallel, perpendicular, or skewed relative to a direction of fluid flow within the lumen 24 of the cannula. An embodiment of a cannula having skewed ribs is shown in FIGS. 9 and 10, and an embodiment of a cannula having perpendicular ribs is shown in FIG. 10A. Such rib 66 shape, size, and orientation may be selected to provide an optimal combination of features for an individual patient or procedure. In addition the individual apertures within the aperture sets 30 can be in line, as best shown in FIG. 7B, or offset from each other as shown best in FIG. 8B to further decrease the likelihood of occlusion.

Rib 66 may comprise a constant or a variable cross-section. As shown in FIG. 8B, rib 66 may include an interior diameter 70 and an exterior diameter 78. In some embodiments, the interior diameter 70 may be less than or equal to the first outer diameter A, and the exterior diameter 78 may be greater than the first outer diameter A. In some embodiments, rib 66 may have a constant interior diameter 70 and a variable exterior diameter 78 having a minimum 84 and a maximum 86. In such embodiments, the interior diameter 70 may be less than the first outer diameter A and at least the maximum 86 of the exterior diameter 78 may be greater than the first outer diameter A.

As shown in FIGS. 11 and 12A-B, in some embodiments, the portion 60 outward of the first outer diameter includes an asymmetrical bulge 100 extending beyond the body outer diameter A. Bulge 100 may be useful for allowing fluids to pass through fluid inlet apertures 30 without becoming occluded by surrounding tissue. Such a bulge 100 may be useful for reducing the likelihood of occlusion of the fluid inlets of smaller diameter.

Figure 13:
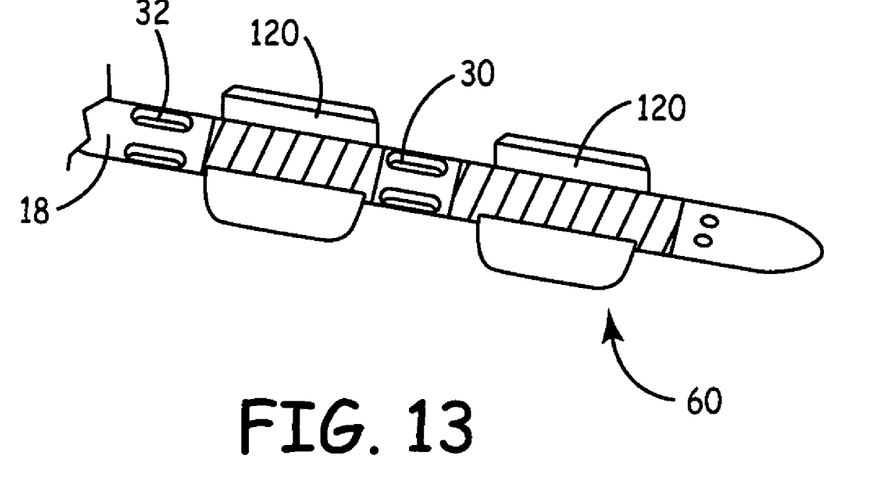
FIG. 13 is a side plan view of a cannula according to an embodiment of the invention.
Figure 14:
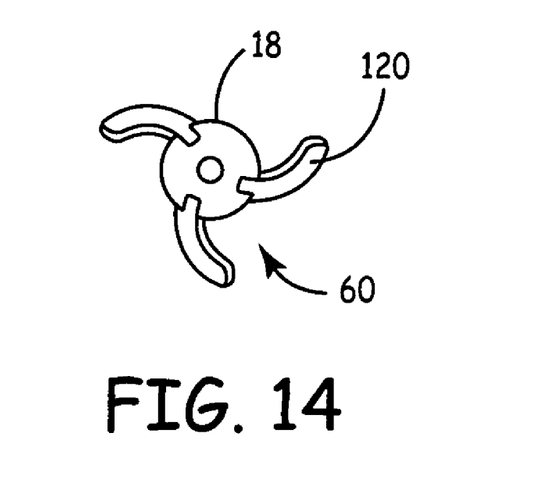
FIG. 14 is an end plan view of a cannula according to an embodiment of the invention.

In some embodiments, the portion 60 outward of the first outer diameter includes a flap 120, as shown in FIGS. 13 and 14. Such flaps may be pivotably coupled to the cannula body 18 and may pivot from an open position to a closed position. Flaps 120 may be positioned over the fluid inlets or spaced a distance along the cannula body from the fluid inlets. It should be noted that even when flaps 120 are in their closed position, fluids may access and pass through apertures 30.

Figure 15:
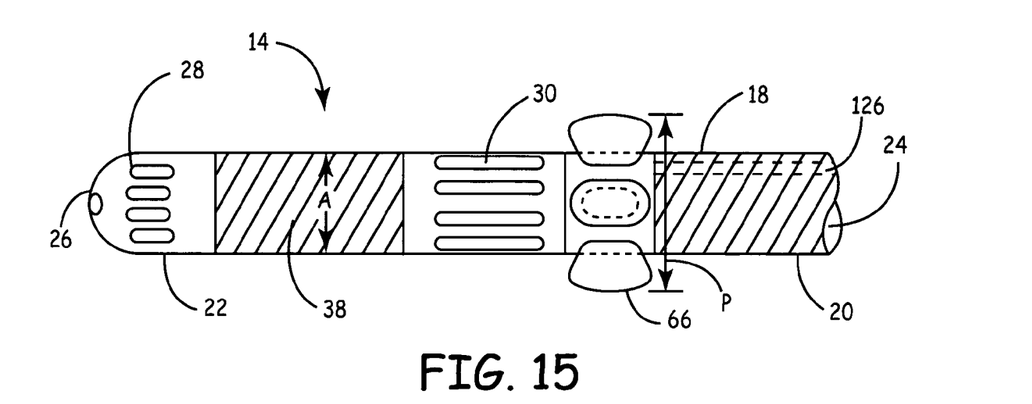
FIG. 15 is a side plan view of a cannula according to an embodiment of the invention.
Figure 16:
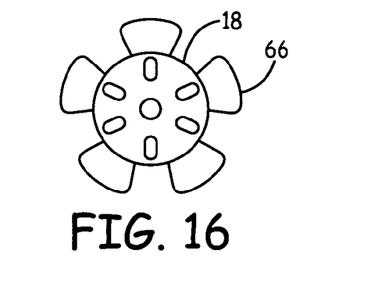
FIG. 16 is an end plan view of a cannula according to an embodiment of the invention.

In some embodiments outward portion 60 may be expandable. In such embodiments, cannula 14 may be placed within the vessel of a patient and the outward portion 60 may be expanded until it reaches a desired diameter. For example, outward portion 60 may be expanded until its diameter is approximately equal to the diameter of the vessel in which the cannula 14 resides. In some embodiments, the outward portion 60 may comprise a balloon (e.g., comprising silicon) that is expanded pneumatically to form a relatively rigid outer portion. In embodiments wherein the outward portion includes ribs 66, each rib 66 may individually comprise an individual balloon that is fed through a common pneumatic omnibus valve. An embodiment of a cannula having pneumatic/balloon ribs is shown in FIGS. 15 and 16. In such embodiments, a second lumen 126 may be provided within the cannula body (e.g., within the wall of the cannula body) to inflate the ribs. A fluid fill line may be spliced into the second lumen, and a syringe may be coupled to the fluid fill line to inflate the ribs 66.

Embodiments of the invention also provide for materials to produce one or more of body 18 and outer portion 60. In some embodiments, the outer portion 60 is rigid relative to the cannula body 18. For example, the outward portion may include a relatively hard and stiff plastic such as a poly vinyl chloride. In other embodiments the outward portion 60 includes a metal. Examples of suitable materials include stainless steel, nitinol, ABS, acrylic, polycarbonate, Ultem,™ polyurethane, glass filled plastics, titanium, and combinations thereof.

In use, any of the various embodiments of cannula 14 described above may be used in a surgical procedure (e.g., a cardiopulmonary bypass procedure) to reduce cannula fluid inlet occlusion. When utilizing a cannula 14 with unsymmetrical ribs 66 and/or bulge 100, the largest portion of the bulge 100 may be placed about 180 degrees from the tricuspid valve within the atrium to maximize the drainage of fluid from the atrium without occluding the fluid inlet.

Thus, embodiments of the CANNULA SYSTEM AND METHOD are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. A cannula comprising a cannula body having a first outer diameter, a proximal end, a distal end, a lumen extending between the proximal and distal ends, and a fluid outlet formed on the proximal end, wherein the cannula body further comprises an outward portion proximal of the distal end and having a second outer diameter greater than the first outer diameter, wherein the outward portion comprises an asymmetrical bulge of a surface of the cannula that further includes at least one rib extending from the surface of the bulge and at least one first fluid inlet aperture that is open through the surface of the bulge, the outward portion being adapted to space tissue from the at least one first fluid inlet aperture to maintain fluid flow.

2. The cannula of claim 1 wherein the at least one first fluid inlet aperture is spaced a first distance from the distal end and wherein the cannula further comprises at least one second fluid inlet aperture spaced a second distance from the distal end.

3. The cannula of claim 1 wherein the outward portion includes a plurality of symmetrical ribs.

4. The cannula of claim 1 wherein the outward portion includes a plurality of asymmetrical ribs.

5. The cannula of claim 1 wherein at least one rib comprises a rib interior diameter and a rib exterior diameter, the rib interior diameter being less than or equal to the first outer diameter and the rib exterior diameter being greater than the first outer diameter.

6. The cannula of claim 1 wherein at least one rib comprises a rib interior diameter that is constant and a rib exterior diameter that is variable having a minimum and a maximum, the rib interior diameter being less than the first outer diameter and at least the maximum of the rib exterior diameter being greater than the first outer diameter.

7. The cannula of claim 1 wherein at least one rib is parallel relative to a direction of fluid flow within the cannula.

8. The cannula of claim 1 wherein at least one rib is perpendicular relative to a direction of fluid flow within the cannula.

9. The cannula of claim 1 wherein at least one rib is skewed relative to a direction of fluid flow within the cannula.

10. The cannula of claim 1 wherein the outward portion is expandable.

11. The cannula of claim 1 wherein the outward portion comprises an expandable balloon.

12. The cannula of claim 1 wherein the outward portion comprises a flap.

13. The cannula of claim 1 wherein the outward portion is rigid relative to the cannula body.

14. The cannula of claim 1 wherein the outward portion comprises a poly vinyl chloride.

15. The cannula of claim 1 wherein the outward portion comprises a metal.

16. A venous cannula comprising a cannula body having a first outer diameter, a proximal end, a distal end, a lumen extending between the proximal and distal ends, a fluid outlet formed on the proximal end, at least one fluid inlet formed proximal of the distal end, wherein the cannula body further comprises a first outward portion comprising an outer diameter greater than the first outer diameter and a first aperture set and a second outward portion comprising an outer diameter greater than the first outer diameter and a second aperture set and at least one rib outward of the first outer diameter having a second outer diameter greater than the first outer diameter, the at least one rib being adapted to space tissue from the aperture sets to maintain fluid flow during kinetically assisted venous drainage.

17. The cannula of claim 16 wherein the first aperture set is spaced a first distance from the distal end and the second aperture set is spaced a second distance from the distal end, the at least one rib being between the first aperture set and the second aperture set.

18. A method of reducing cannula fluid inlet occlusion comprising contacting a patient with a cannula having a body with a first outer diameter, a proximal end, a distal end, a lumen extending between the proximal and distal ends, a fluid outlet formed on the proximal end, wherein the body further comprises an outward portion proximal of the distal end and having a second outer diameter greater than the first outer diameter, wherein the outward portion comprises an asymmetrical bulge of a surface of the cannula that further includes at least one rib extending from the surface of the bulge and at least one fluid inlet aperture that is open through the surface of the bulge, the outward portion adapted to space tissue from the at least one fluid inlet aperture to maintain fluid flow, wherein at least the distal end and the outward portion are positioned within the patient.

* * * * *